United States Patent [19]

Blytas

[11] Patent Number: 4,704,463

[45] Date of Patent: Nov. 3, 1987

[54] PROCESS FOR THE PRODUCTION EPICHLOROHYDRIN

[75] Inventor: George C. Blytas, Houston, Tex.

[73] Assignee: Shell Oil Company, Houston, Tex.

[21] Appl. No.: 866,804

[22] Filed: May 27, 1986

[51] Int. Cl.$^4$ ........................................... C07D 301/26
[52] U.S. Cl. .................................... 549/521; 549/541; 568/847
[58] Field of Search ................. 549/521, 541; 568/847

[56] References Cited

U.S. PATENT DOCUMENTS 2,714,121 7/1955 Anderson et al. .................... 568/847
2,714,123 7/1955 Johnson .............................. 568/847

Primary Examiner—Norma S. Milestone
Attorney, Agent, or Firm—Ronald R. Reper

[57] ABSTRACT

A process for the production of epichlorohydrin is disclosed which comprises reacting allyl chloride, chlorine and water to form an intermediate, then rapid conversion and separation of epichlorohydrin product; the epichlorohydrin-depleted reaction mixture is cooled and subjected to electrodialysis then reverse osmosis to concentrate and remove deleterious by-products, and at least a substantial portion of the resultant permeate is recycled to the reaction zone, thereby enabling reduced operating costs and/or improved yield.

8 Claims, 1 Drawing Figure

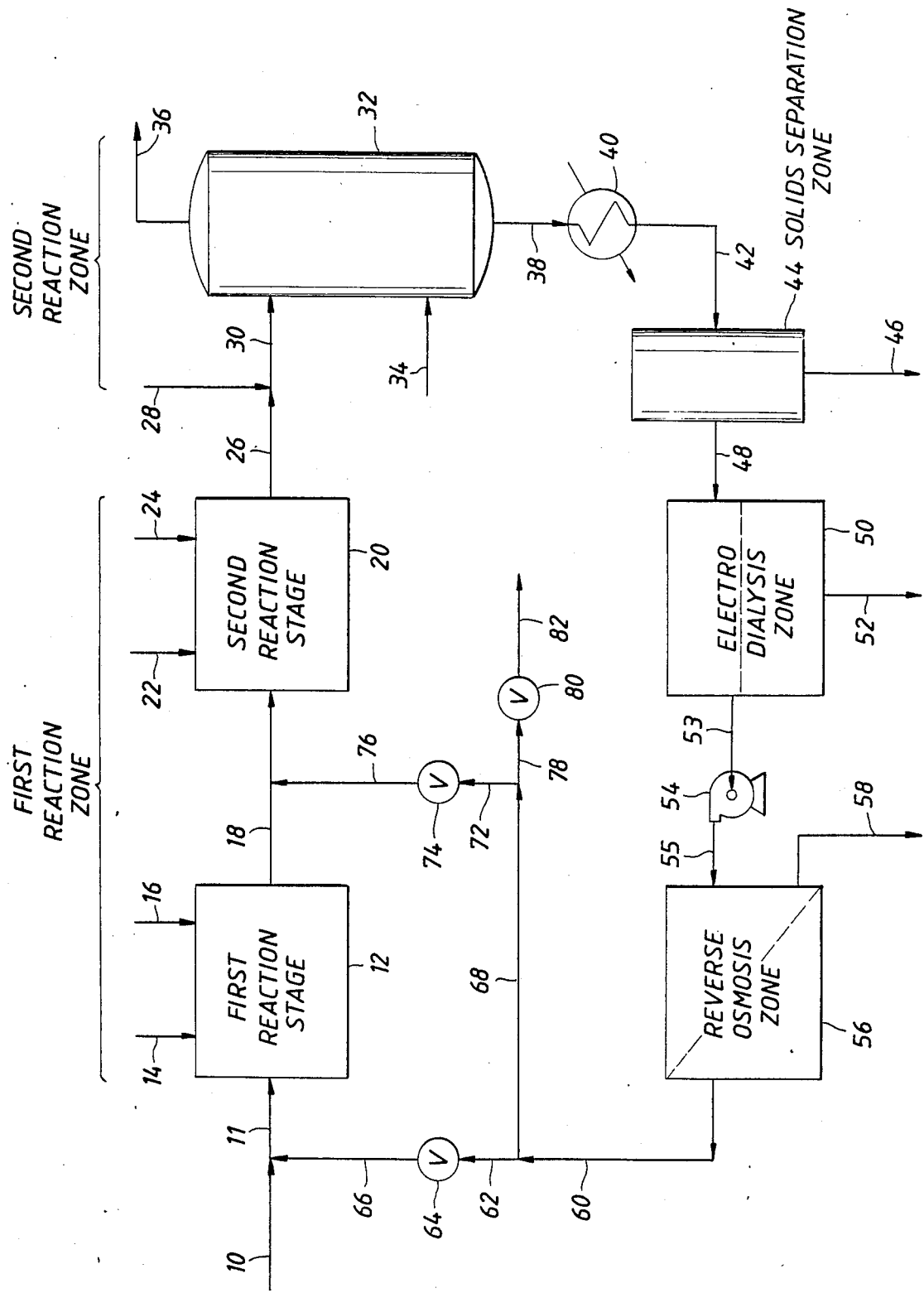

PROCESS FOR THE PRODUCTION EPICHLOROHYDRIN

BACKGROUND OF THE INVENTION

This invention relates to an improved process for the production of epichlorohydrin i.e., -chloropropylene oxide. Conventionally epichlorohydrin is produced by the dehydrohalogenation of dichlorohydrin. The dichlorohydrins i.e., 2,3 dichloro-1-propanol and 2,3 dichloropropanol, herein collectively called dichlorohydrin, may be prepared by reacting chlorine, water and allyl chloride in high dilution of e.g., 250 to 400 volumes of water per volume of e.g., halohydrocarbon as disclosed in U.S. Pat. No. 2,714,121, incorporated by reference.

It is known from U.S. Pat. No. 2,177,419, incorporated herein by reference, that epichlorohydrins such as epichlorohydrin may be prepared by reacting a dihalohydrin with a basic substance in the presence of water and rapid separation of the product from the reaction mixture by flash distillation, to minimize formation of other organic compounds.

A disadvantage of such processes is that after removal of the epichlorohydrin product there remains a substantial quantity of water containing a considerable concentration of inorganic salts and smaller but significant quantities of organic compounds. particularly halogen-containing organics such as tetrachloropropyl ether, trichloropropane and the like which must be removed prior to discharge to receiving bodies of water such as rivers and lakes.

It has now been found that advantages selectivity to the desired epichlorohydrin can be retained while reducing the amount of water consumed in the process, and enabling significant reduction in the quantity of aqueous waste that must be treated by using a sequence of electrodialysis and reverse osmosis steps to separate undesirable materials from the final reaction mixture, and recycling a portion of the permeate thus obtained to the dichlorohydrin reaction zone.

SUMMARY OF THE INVENTION

According to the invention there is provided a continuous process for the producton of epichlorohydrin which comprises in sequence (a) reacting allyl chloride, chlorine and water in a first reaction zone to produce an aqueous solution of dichlorohydrin,
(b) reacting said dichlorohydrin solution with an excess of a basic substance in a second reaction zone under conditions of temperature and contact time of the reactants whereby the dichlorohydrin is substantially converted to epichlorohydrin.
(c) separating the formed epichlorohydrin rapidly and substantially completely from the aqueous reaction mixture as overhead by flash distillation,
(d) cooling said reaction mixture depleted in epichlorohydrin to a temperature below about 70° C.,
(e) electrodialyzing said cooled reaction mixture in an electrodialysis zone to afford (1) an electrodialysis concentrate stream having an inorganic chloride content higher than said cooled reaction mixture feed to the electrodialysis zone, and (2) a diluate stream containing organic chloride compounds and having a lower inorganic chloride content than said reaction mixture feed,
(f) removing said concentrate stream of step (e),
(g) subjecting said diluate stream to reverse osmosis to form a retentate stream having a higher content of organic and inorganic chlorides than said diluate stream, and permeate stream substantially depleted in both organic and inorganic chlorides,
(h) removing said retentate stream, and
(i) recycling at least part of said permeate stream to said first reaction zone.

THE DRAWING

The figure depicts a schematic flow diagram of a preferred embodiment of the invention.

DESCRIPTION OF PREFERRED EMBODIMENTS

According to the invention allyl chloride, water and chlorine are reacted to form dichlorohydrin which is then reacted with base to form epichlorohydrin, the epichlorohydrin is removed and the epichlorohydrin-depleted reaction mixture is processed to remove by-products and/or materials that would adversely impact selectivity to the desired epichlorohydrin product from the starting allyl chloride, water and chlorine. It is an advantage of the present invention that the by-products and/or materials that would adversely affect selectivity to epichlorohydrin are removed in concentrated form, thereby facilitating disposal and/or processing for further use.

In the process allyl chloride, water and chlorine are reacted in a first reaction zone to produce an aqueous solution of dichlorohydrin. This dichlorohydrination reaction takes place readily at temperatures in the range from about 15° to about 55° C. For maximum dichlorohydrin yield it is necessary to run at low concentration of both chloride ion and dichlorohydrin. As described in U.S. Pat. No. 2,714,121 the reaction may be carried out at high water dilution in a reaction zone comprising a stirred reaction vessel or a loop reactor. Preferably the reaction zone comprises a plurality of reaction stages arranged in series flow. A particularly preferred mode of operation is to feed substantially all the water to the first of the reaction stages and add the other reactants in substantially equimolar proportions to the first and to each of the subsequent reaction stages, as disclosed in the U.S. Pat. No. 2,714,123 incorporated herein by reference.

The first reaction zone effluent typically has a low pH value resulting from the hydrogen chloride formed as by-product in the series of chemical reactions. Organic by-products typically present in said reaction zone effluent include trichloropropane and tetrachloropropylether.

The dichlorohydrin-containing effluent from the first reaction zone is passed to the second reaction zone where it is reacted with an excess of a basic substance under conditions of temperature and contact time of the reactants whereby the dichlorohydrin is substantially converted to epichlorohydrin at a practical rate, while the undesirable side reactions such as hydrolysis and hydration of the epichlorohydrin are substantially obviated.

Although in theory any basic substance can be employed, preference is given to hydroxides and carbonates of alkali metals and/or alkaline earth metals. Particularly preferred because of their availability and generally lower cost are caustic soda (sodium hydroxide), lime (calcium hydroxide), and limestone (calcium carbonate).

In the second reaction zone, it is preferred that the epichlorohydrin product remain in contact with the aqueous alkaline reaction mixture for the absolute minimum of time and is rapidly removed by flash distillation at atmospheric or superatmospheric pressure. The second reaction zone suitably comprises a conventional flash distillation apparatus such as a film evaporator or stripping column. In a preferred mode using a stripping column, the first reaction zone effluent is continuously fed into said column under at least atmospheric pressure where it is contacted with live steam. The epichlorohydrin is rapidly separated from the reaction mixture and is removed from the upper portion of the column along with water and any unchanged dichlorohydrin that may be present. Typically the epichlorohydrin is removed as an azeotrope with water. The epichlorohydrin-depleted reaction mixture is discharged from the base of the column.

The reaction mixture after separation of the epichlorohydrin will ordinarily have a temperature in excess of about 80° C. e.g., 100°–110° C. According to the invention the mixture is cooled to a temperature below about 80° C. in order to protect the service life of the membranes employed in the subsequent process steps. Preferably, the reaction mixture depleted in epichlorohydrin is cooled by indirect heat exchange to a temperature in the range from about 35° to about 60° C.

Optionally, the cooled epichlorohydrin-depleted reaction mixture may be subjected to a solids removal step to remove any undissolved materials from said mixture so as to minimize fouling of the membranes in the subsequent processing steps. When there are substantial amounts of solids present, e.g., when a lime slurry is employed as the basic substance, the solids removal step may comprise any known technique such as sedimentation, centrifugation, and filtration. Microporous ultrafiltration is preferred. A number of suitable ultrafiltration systems are commercially available. Any separated solids may be removed from the process, however, as the solids typically comprise mostly basic substance, they may be recycled to the reaction step (b) of the present process. After the solids removal step, when employed, the cooled reaction mixture is fed to an electrodialysis zone.

In the electrodialysis zone the reaction mixture feed is electrodialyzed to afford: (1) an electrodialysis concentrate stream having an inorganic chloride content greater than said feed, and (2) a diluate stream containing organic chloride compounds and having a lower inorganic chloride content than said feed.

Electrodialysis is by now a well established industrial process. Basically, an electrodialysis unit comprises a plurality of membranes alternately anionic and cationic placed between an anode and a cathode connected to a direct current source. The membranes are usually separated from each other by 1 to 5 mm using appropriate spacers and the feed stream may be made to flow through a spacer creating a tortuous path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

If a feed stream is introduced uniformly from the top of the electrodialysis unit, it will be found that passages in the unit having an anion membrane on the cathode side of the passage and vice versa will become concentrate streams richer in ionized (herein saline) components and the other stream in passages bounded by anion membranes on the anode side and cathode membranes on the cathode side will become depleted in ionized components. Such depleted stream or streams are herein referred to as the diluate stream.

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volume of diluate/concentrate streams.

The anioic and cationic membranes employed herein are known in the art. Generally, the anionic and cationic membranes comprise flat sheets of inorganic or organic materials which have extreme water-insolubility. Preferably the anionic and cationic membranes are prepared from synthetic organic resinous, polymeric materials, (e.g., polystyrene polymers) to which are bonded ionic groups. Any strong or weak base (e.g., tertiary amines or quaternary ammonium compounds) can be chemically bonded to the organic material to from cationic membranes; any strong or weak acid (e.g., aryl sulfonates) can be chemically bonded to the organic resinous material to form anionic membranes.

Generally, the anionic and cationic membranes herein, either in the form of laminate or a homogeneous cast or sheet, are "backed" or reinforced with an imbedded screen or matrix of synthetic reinforcing fabric, for example, Dynel, a vinylidene copolymer, or fiberglass to provide them with a substantially rigid structure. Other 'backings' can be used, provided the anionic and cationic membranes remain essentially impervious to mass flow but porous enough to permit ion migration or transfer.

The cation and anion-exchange membranes can be any cationand anion-selective membranes respectively which are essentially stable in the feed water and not chemically degraded by the components therein. Exemplary membranes are disclosed in the article entitled "Electrodialysis", Kirk-Othmer, Encyclopedia of Science and Technology, pages 846–865 (Second Edition, Interscience Publishers, 1965) and U.S. Pat. Nos. 2,730,768, 2,762,272, 2,860,097 and 3,616,385 incorporated herein by reference.

Generally, for stability of the membranes, it is necessary to employ temperatures below about 70° C. during electrodialysis, while in terms of electrical efficiency it would be preferred to carry out the electrodialysis step below about 55° C., especially at a temperature in the range from about 20° to 50° C.

The diluate stream from the electrodialysis step has greatly reduced ion content and is subjected to reverse osmosis in a reverse osmosis zone to form a retentate stream having a higher content of organic and inorganic chlorides than said diluate stream, and a permeate stream of relatively pure water, i.e., substantially depleted in both organic and inorganic chlorides. The retentate stream is removed from the reverse osmosis zone for further treatment and/or disposal. At least part of the permeate stream is recycled to the first reaction zone. It is preferred that at least about 50% by volume of the permeate, and more preferably at least about 75% by volume of the permeate is recycled to said first reaction zone. In a particularly preferred embodiment wherein the first reaction zone comprises a plurality of e.g., two or more, reaction stages, the permeate is recycled to the first of such reaction stages.

The reverse osmosis membranes used in the reverse osmosis step may require some care in selection, since they are required to retain the organics in the osmotic concentrate stream. A conventional polysulfone membrane has been found useful for this purpose as have thin film composite membranes.

An embodiment of the invention will be described with reference to the figure which shows diagrammatically a preferred assemblage according to the invention. In the figure a fresh water stream is continuously introduced through conduit 10 and recycled water through conduit 11 at a total rate of about 1100 gpm into a first reaction stage 12 of the first reaction zone. Of these 1100 gpm, only about 300 gpm is fresh water, and 800 gpm is recycled from the downstream process. Allyl chloride is continuously fed into said first reaction stage through conduit 14, while chloride in an amount substantially equimolar with respect to the allyl chloride is fed via conduit 16. The reaction mixture is circulated at a high rate and at a temperature of about 55° C. in said first stage. Effluent from said first stage comprising about 0.2 M dichlorohydrin and about 0.2 N HCl is passed through conduits 17 and 18 to second reaction stage 20. As with the previous reaction stage allyl chloride is continuously fed into the rapidly circulated reaction mixture through conduit 22 and a substantially equimolar amount of chlorine through conduit 24. The reaction is mildly exothermic. The second stage reaction mixture containing about 0.4 M dichlorohydrin and about 0.4 N HCl and having a temperature less than 60° C. is passed via conduit 26 to the second reaction zone. A basic substance such as concentrated NaOH is added via conduit 28 and the dichlorohydrin is rapidly converted to epichlorohydrin in conduit 30 and stripper column 32. To permit this reaction, enough NaOH is added to neutralize all HCl, and additionally, to react with all of the dichlorohydrin coverting it to epichlorohydrin. Live steam is added via conduit 34 and the epichlorohydrin is rapidly separated as an azeotrope with water overhead fraction via conduit 36. The epichlorohydrin-depleted reaction mixture having a temperature of about 100°–110° C. is passed from the bottom of stripper column 32 via conduit 38 to cooler 40 where it is cooled to a temperature below about 70° C. The cooled reaction mixture is then passed via conduit 42 to solids separation zone 44 which may be a filter press, deep-bed filtration unit or a sedimentation clarifier unit with associated coagulation/flocculation units. Preferably it is an ultrafiltration unit with e/.g., a polysulfone membrane. Good results have been achieved with a membrane having a nominal flux of 150 GFD at 50 psi in distilled water. Separated solids are removed from said zone 44 via conduit 46, and the solids-free reaction mixture is passed via conduit 48 to electrodialysis zone 50. Electrodialysis zone 50 is comprised of alternating anionic exchange membranes designated as 203 QZL-386 and cationic exchange membranes designated as 61 CZL-386, which membranes are commercially available for Ionics, Inc., Watertown, Mass. Typically the voltage across each stack of membranes is arranged so that there is a voltage of about 0.5 to about 3.0 volts per cell pair, with a voltage in the range from about 1.0 to about 2.5 being preferred. The ionic materials in the reaction mixture are removed into a concentrate stream which exits the unit via line 52. From electrodialysis zone 50 a diluate stream containing less than about 1000 ppm of ionic material and substantially all of the organic compounds from the second reaction zone is passed via conduit 53, pump 54 and conduit 55 to reverse osmosis zone 56.

Reverse osmosis zone 56 contains a commercially available thin film composite membrane. The feed enters said zone at a pressure of about 400 psi resulting (1) in a retentate stream containing substantially all of the organics and inorganics present in the feed stream in an amount of water which is only about 3 to 5 percent of the feed volume, and (2) a permeate stream of relatively pure water containing less than about 100 ppm of organics. The permeate stream is passed via conduits 60, 62, valve 64 and conduits 66 and 11 to first reaction stage 12. If desired, part of said permeate stream may be directed through conduits 68 and 72, valve 74 and conduits 76 and 18 into second reaction stage 20. Alternately, a portion of said permeate may be removed via conduits 68 and 78, valve 80 and conduit 82 to be recycled to other parts of the process (not shown) such as slurrying lime, when lime is the basic substance used in the process.

What is claimed is:

1. A continuous process for the production of epichlorohydrin which comprises in sequence
   (a) reacting allyl chloride, chlorine and water in a first reaction zone to produce an aqueous solution of dichlorohydrin,
   (b) reacting said dichlorohydrin solution with an excess of a basic substance in a second reaction zone under conditions of temperature and contact time of the reactants whereby the dichlorohydrin is substantially converted to epichlorohydrin,
   (c) separating the formed epichlorohydrin rapidly and substantially completely from the aqueous reaction mixture as overhead by flash distillation,
   (d) cooling said reaction mixture depleted in epichlorohyrin to a temperature below about 70° C.,
   (e) electrodialyzing said cooled reaction mixture in an electrodialysis zone to afford: (1) an electrodialysis concentrate stream having an inorganic chloride content higher than said cooled reaction mixture feed to the electrodialysis zone, and (2) a diluate stream containing organic chloride compounds and having a lower inorganic chloride content than said reaction mixture feed,
   (f) removing said concentrate stream of step (e),
   (g) subjecting said diluate stream to a reverse osmosis to form a retentate stream having a higher content of organic and inorganic chlorides than said diluate stream, and a permeate stream substantially depleted in both organic and inorganic chlorides,
   (h) removing said retentate stream, and
   (i) recycling at least part of said permeate stream to said first reaction zone.

2. A process as in claim 1 wherein after step (d), said cooled reaction mixture is subjected to an ultrafiltration step to separate any insoluble material and afford a filtrate depleted in insoluble material, and said filtrate is passed as feed to the electrodialysis zone of step (e).

3. A process as in claim 1 wherein said basic substance is selected from the group consisting of hydroxides and carbonates of metals selected from the group consisting of alkali metals and alkaline earth metals.

4. A process as in claim 1 wherein step (b) said basic substance is selected from caustic soda, lime and limestone.

5. A process as in claim 1 wherein step (a) the first reaction zone comprises a plurality of reaction stages arranged in series flow, and said permeate from step (i) is recycled to the first of such reaction stages.

6. A process as in claim 1 wherein step (d) said reaction mixture is cooled to a temperature in the range from about 35° to about 60° C.

7. A process as in claim 1 wherein at least about 50% of said permeate stream is recycled to said first reaction zone.

8. A process as in claim 1 wherein at least about 75% of said permeate stream is recycled to said first reaction zone.

* * * * *